(12) United States Patent
Müller-Fiedler et al.

(10) Patent No.: US 7,279,759 B2
(45) Date of Patent: Oct. 9, 2007

(54) MEMBRANE SENSOR

(75) Inventors: Roland Müller-Fiedler, Leonberg (DE); Hans Hecht, Korntal-Muenchingen (DE); Joerg Muchow, Reutlingen (DE); Matthias Fuertsch, Gomaringen (DE); Andreas Stratmann, Gomaringen (DE); Heribert Weber, Nuertingen (DE); Winfried Bernhard, Gerlingen (DE); Detlef Gruen, Reutlingen (DE); Andreas Duell, Stuttgart (DE); Rainer Schink, Leonberg (DE); Ulrich Wagner, Stuttgart (DE); Christoph Schelling, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/547,041

(22) PCT Filed: Feb. 18, 2004

(86) PCT No.: PCT/DE2004/000295

§ 371 (c)(1),
(2), (4) Date: Feb. 13, 2006

(87) PCT Pub. No.: WO2004/080885

PCT Pub. Date: Sep. 23, 2004

(65) Prior Publication Data

US 2006/0197634 A1 Sep. 7, 2006

(30) Foreign Application Priority Data

Mar. 11, 2003 (DE) ................ 103 10 859
Jun. 13, 2003 (DE) ................ 103 26 786
Dec. 11, 2003 (DE) ................ 103 57 869

(51) Int. Cl.
*H01L 27/14* (2006.01)
*H01L 29/82* (2006.01)
*H01L 29/84* (2006.01)

(52) U.S. Cl. .................... 257/414; 257/417
(58) Field of Classification Search ........... 257/414, 257/417

See application file for complete search history.

(56) References Cited

U.S. PATENT DOCUMENTS 5,705,745 A * 1/1998 Treutler et al. .......... 73/204.26

FOREIGN PATENT DOCUMENTS

| DE | 40 24 780 | 10/1991 |
|----|-----------|---------|
| DE | 42 15 722 | 11/1993 |
| DE | 195 27 861 | 1/1997 |
| DE | 199 51 595 | 5/2001 |
| DE | 19951595 A * | 5/2001 |
| DE | 102 10 335 | 10/2003 |

* cited by examiner

*Primary Examiner*—Jerome Jackson
*Assistant Examiner*—Anthony Ho
(74) *Attorney, Agent, or Firm*—Kenyon & Kenyon LLP

(57) ABSTRACT

A micromechanical sensor and a method for manufacturing a micromechanical sensor which has at least one membrane are provided. The membrane is made of a first material which is accommodated in a surrounding second material, and the membrane is configured for sensing a medium surrounding it. The membrane is reinforced, at least partly, by a third material at break-sensitive points on the membrane rim. Reinforcement of the membrane rim increases the stability and thus also the service life of the membrane and the sensor.

13 Claims, 1 Drawing Sheet

MEMBRANE SENSOR

CROSS-REFERENCE TO RELATED APPLICATIONS:

This national phase patent application claims the benefit of and priority to PCT International Application No. PCT/DC2004/000295, filed Feb. 18, 2004, and of German Patent Application No. 10310859.9, which was filed in the German Patent Office on Mar. 11, 2003.

FIELD OF THE INVENTION

The present invention relates to a membrane sensor, in particular a sensor having direct media contact such as a mass air flow sensor, an air pressure sensor, or an air quality sensor.

BACKGROUND INFORMATION

The manufacture of membrane sensors is carried out by depositing the membrane materials, made of silicon oxide, silicon nitride, polysilicon, or metals, for example, on a silicon wafer and subsequent local wet or dry chemical etching of the silicon from the backside up to the membrane. For reducing the heat conduction into the substrate, these sensors frequently have a very thin membrane.

Such a sensor is described in published German patent document DE 42 15 722, for example, in which the membrane is provided with an elastic enclosure for reducing the sensitivity toward the occurring notch tensions on the membrane mounting and for improving the pressure sensitivity. The elastic enclosure is attached opposite the side of the membrane on which the measuring elements are situated and where the medium to be measured flows past.

In these types of sensors having direct media contact, such as the above-mentioned mass air flow sensor, air pressure sensor, or air quality sensor, the membrane, having a thickness in the micrometer range and lateral dimensions from a few 100 micrometers to several millimeters, is directly exposed to the flowing medium, e.g., air. The particles such as dust, contained in the media despite the use of filters, may thus cause damage to the membrane due to the direct bombardment of the membrane with the particles at relatively high flow speeds. Likewise, unfavorable pressure conditions may result in the fact that the membrane of an air pressure sensor experiences too great a deflection. It has been found that, due to the cases indicated, the membrane is susceptible to damage mainly at the break-sensitive membrane rim. Damage to the membrane may range from impairment of the measuring sensitivity to total failure due to the sensor's destruction.

The stability of the membranes against particle bombardment is determined via the statistical service life in an air flow having a defined dust quantity. An increase in stability could be achieved by increasing the membrane thickness and/or by lowering the pre-stressing of the membrane; an increase in the thickness, however, results in an increase in heat conductivity and thus in a deterioration of the characteristic curve. As a rule, pre-stressing cannot be sufficiently lowered since, to prevent bulging, the membrane must remain in the tensile stress range under all operating conditions.

The membrane thickness in air pressure sensors may also be varied only to a certain degree since thickening of the membrane involves the displacement of the measurable pressure range.

German patent document DE 102 10 335 describes a membrane sensor whose membrane is situated in a mounting on the sensor housing. In addition to this mounting, the sensor has an additional layer on the membrane rim with which the stability of the membrane against impacting particles is increased.

SUMMARY

The present invention provides a micromechanical sensor and a method for manufacturing a micromechanical sensor which has at least one membrane which is made of a first material in such a way that it is accommodated in a second material for sensing a medium surrounding it. The present invention also provides that the membrane is at least partly reinforced at the membrane rim at break-sensitive points using a third material. The stability and thus the service life of the membrane or the sensor are increased due to the reinforcement of the membrane rim.

In an example embodiment of the present invention, it is provided that, for increasing the stability, the membrane has a membrane thickness which is dependent on the proximity to the membrane rim. It is possible, for example, that the thickness of the membrane increases toward the membrane rim.

An example embodiment of the present invention provides that the membrane is made of the first and the third material. While the first material has a uniform layer thickness across the entire membrane, the third material may assume different layer thicknesses in the membrane, as described in the above embodiment.

In order to achieve an increase in membrane stability with regard to the stress during a measuring sequence, the membrane rim on the side of the membrane which is exposed to the medium to be sensed may be covered with the third material at least at selected points. If the membrane edges, for example, are completely covered by a layer made of a plastic and elastic third material, this layer is able to absorb the stresses on the membrane without permitting damage to the membrane.

Moreover, this covering makes a selective reinforcement of the membrane possible without a large-area coverage of the membrane rim.

In addition, the membrane incorporates additional structures made of the third material. These structures are designed in such a way that they extend out of the membrane, onto the second material enclosing the membrane, for example. An example embodiment of the present invention utilizes these structures in order to detect performance quantities of the medium and to relay them to an analyzer circuit. This may be achieved, for example, via the measurement of a resistance change in the structures as a function of the performance quantities of the medium.

The third material, with which at least part of the membrane rim is covered, is advantageously electrically conductive. According to the present invention, the covering of the membrane rim and/or the structures may be used as printed conductors and/or other resistance structures due to the conductivity of the third material.

The extension of the structures beyond the membrane rim becomes advantageous in particular when the edges of the structures are situated perpendicular to the membrane rim. Stresses, which also act perpendicular to the membrane rim due to overpressure or due to particles, may be optimally compensated by such a configuration.

According to the present invention, the first, second, and third materials may be composed of different substances.

However, it may be provided that two or even all three materials are composed of the same substance. In an example embodiment of the present invention, silicon, silicon oxide, silicon nitride, and/or a dielectric substance are provided as the substance of at least one of the three materials. It is provided in an example embodiment of the present invention that the third material is composed of platinum, nickel, and/or polysilicon.

The membrane sensor according to the present invention may be used to detect the pressure, the temperature, the composition, the density, or the particle velocity of the medium as the performance quantities of the medium.

DETAILED DESCRIPTION

Tests of membrane sensors have shown that the membrane rim primarily has to bear the stress of a measured value pickup, whereas the membrane center is relatively immune to damage. This is easily comprehensible, since, in a pressure sensor for example, the movement of the membrane results in a strain at the membrane rim which must be compensated via the enclosure of the membrane. A movement of the membrane also occurs in a mass air flow sensor which is caused by the air (or another medium to be measured) flowing past the membrane.

A possible approach to minimize the stress at the membrane rim is to optimally coordinate the layer thicknesses and the layer tensions of the individual layers which make up the membrane and the enclosure surrounding it. However, these parameters may not be varied arbitrarily since they have an effect on the functionality of the components (e.g., heat output, layer cohesion). For this reason, the layout of printed conductors 2 and 3 is optimized at the membrane rims in the present exemplary embodiment according to FIG. 1 in such a way that the elasticity of membrane 1 vis-à-vis static or dynamic stress is greatly increased. This optimization may take place by covering membrane 1 and part of the membrane's enclosure with printed conductors 2 and 3 on two opposite sides, for example. Covering the membrane rims with a resistance or printed conductor structure as completely as possible is another possibility. The plastically and elastically deformable layer formed by the resistance or printed conductor structures may thus absorb stresses without permitting damage to membrane 1.

In addition to the membrane rims, the structures which are situated on the surface of membrane 1 are also exposed to stresses caused by the measured value pickup. Structures 4, 6, 9, and 10 shown in FIGS. 2 and 3 on the membrane surface may be implemented, for example, as resistance or printed conductor structures which detect measured variables via the movement of the membrane or the passing flow of the air particles. The detected measured variables represent performance quantities such as the pressure, the temperature, the composition, the density, or the flow velocity of the medium to which the membrane is exposed. In order to relay these measured variables to an analyzer circuit it is necessary to establish a connection from the structures across the membrane rim to the analyzer circuit. Since this connection crosses the critical membrane rim, optimization of this connection needs to be considered.

Figure 1:
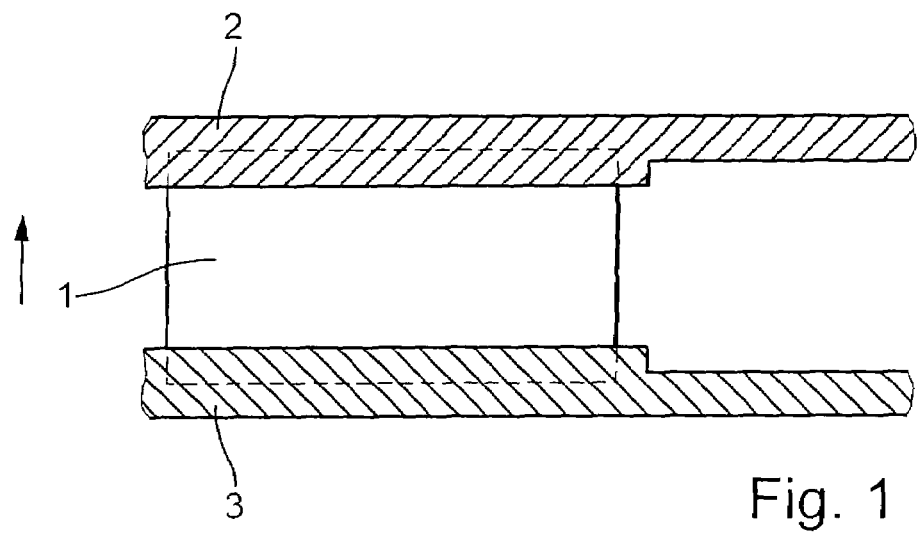
FIG. 1 shows a printed conductor covering the membrane rim.
Figure 2:
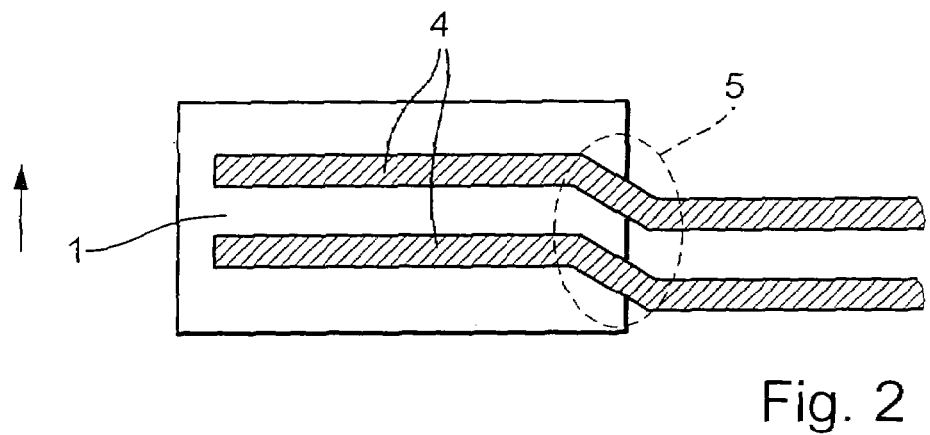
FIG. 2 shows an example for guiding the resistance structures on the membrane surface.
Figure 3:
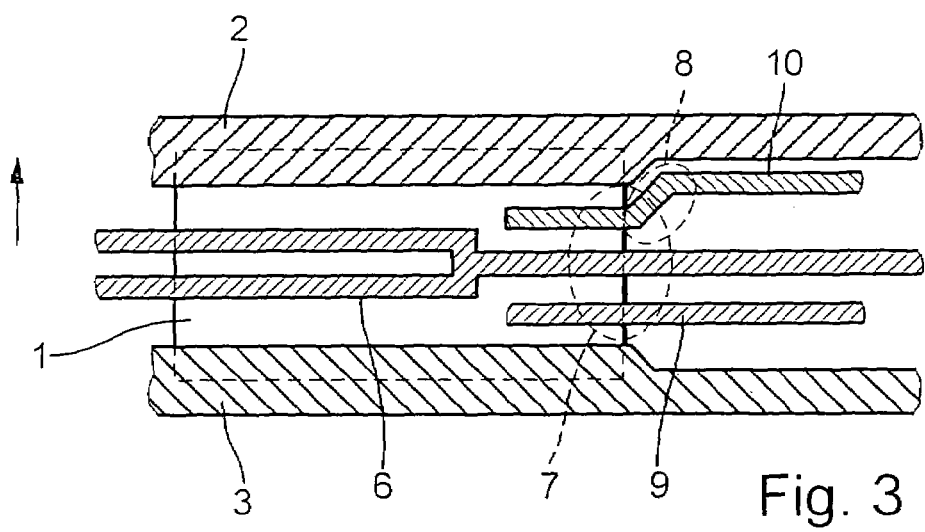
FIG. 3 shows an optimized coverage of the membrane with resistance and printed conductor structures.

In mass air flow sensors, the air (or another medium to be measured) flows along the sensor in one direction, as indicated by an arrow in FIGS. 1 through 3, as an example. In addition to the stress on the membrane rims due to the movement of the membrane, the fast air particles flowing past the membrane also cause a bombardment of the resistance structures which lead from the membrane to analyzer circuits. In particular, in a resistance structure as illustrated in FIG. 2 in section 5, damage to the structures or printed conductors, leading away from the membrane, cannot be ruled out. However, since structure section 5 provides the flowing particles with a large area of interaction, damage to the structures may be reduced by minimizing this area of interaction. An example of implementing this is illustrated in section 7 of FIG. 3. All resistance structures or printed conductors 6, 9, and 10 rest perpendicularly on the respective membrane rim, thereby offering the particle flow a minimal area of action. For relaying the variables detected by the resistance structures, the printed conductors, after having left membrane 1 as shown in section 8, may again be angled in order to guide them away out of the area of the air flow. Installing the printed conductor structures according to section 7 has the further advantage that stresses on the printed conductor structures, caused, for example, by overpressure or a particle flow, also act perpendicular to the membrane rim. The stresses may thus be optimally compensated, whereas in inclined structures, as shown in section 5 of FIG. 2, complete compensation is not possible.

The configuration of membrane sensors using the technology of silicon micromechanics may be based on a defined sequence of dielectric layers (e.g., silicon oxide and silicon nitride), optionally of silicon, and optionally of materials for the resistance measurement (e.g., platinum, nickel, polysilicon). On the membranes manufactured in this way, structures are frequently provided for measuring resistances, for example.

What is claimed is:

1. A micromechanical sensor, comprising:
   a membrane including a first material, the membrane being enclosed, at least partly at a rim of the membrane, by a second material surrounding the membrane, wherein the membrane is exposed to a medium to be sensed, and a third material provided at least on a part of the membrane rim;
   wherein the third material reinforces the membrane against stresses caused by the medium to be sensed, thereby increasing stability;
   wherein the membrane includes at least one structure that extends beyond the membrane rim, the at least one structure having the same composition as the third material, and wherein the at least one structure provides resistance measurements corresponding to performance quantities of the medium.

2. The sensor as recited in claim 1 wherein the membrane has a thickness that varies depending on the proximity to the rim, and wherein the membrane thickness increases toward the membrane rim.

3. The sensor as recited in claim 1 wherein the first material of the membrane has a uniform thickness across the entire membrane surface.

4. The sensor as recited in claim 1 wherein the third material that reinforces the membrane includes a covering provided on a side of the membrane exposed to the medium to be sensed.

5. The sensor as recited in claim 4, wherein the third material is conductive, and wherein the covering is at least a part of at least one of a printed conductor structure and a resistance structure.

6. The sensor as recited in claim 5, wherein at least one of the first, the second and the third material is made of at least one of silicon, silicon oxide, silicon nitride, and a dielectric substance.

7. The sensor as recited in claim 5, wherein the third material is made of at least one of platinum, nickel, polysilicon, and a plastically and elastically deformable material.

8. The sensor as recited in claim 1, wherein the at least one structure is conductive and at least a part of at least one of a printed conductor structure and a resistance structure.

9. The sensor as recited in claim 8, wherein the performance quantities of the medium includes at least one of pressure, temperature, composition, density, and flow rate of the medium.

10. The sensor as recited in claim 1, wherein the performance quantities of the medium includes at least one of pressure, temperature, composition, density, and flow rate of the medium.

11. A micromechanical sensor, comprising:
a membrane including a first material, the membrane being enclosed, at least partly at a rim of the membrane, by a second material surrounding the membrane, wherein the membrane is exposed to a medium to be sensed, and a third material provided at least on a part of the membrane rim;
wherein the third material reinforces the membrane against stresses caused by the medium to be sensed, thereby increasing stability;
wherein the third material that reinforces the membrane includes a covering provided on a side of the membrane exposed to the medium to be sensed;
wherein the third material is conductive, and wherein the covering is at least a part of at least one of a printed conductor structure and a resistance structure;
wherein the portion of the at least one structure that extends beyond the membrane rim extends perpendicular to the membrane rim.

12. The sensor as recited in claim 11, wherein at least one of the first, the second and the third material is made of at least one of silicon, silicon oxide, silicon nitride, and a dielectric substance.

13. The sensor as recited in claim 11, wherein the third material is made of at least one of platinum, nickel, polysilicon, and a plastically and elastically deformable material.

* * * * *